United States Patent
Sanai et al.

(10) Patent No.: US 9,326,787 B2
(45) Date of Patent: May 3, 2016

(54) ENERGY TREATMENT INSTRUMENT

(75) Inventors: Hideo Sanai, Hachioji (JP); Mitsumasa Okada, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 1041 days.

(21) Appl. No.: 13/364,694

(22) Filed: Feb. 2, 2012

(65) Prior Publication Data

US 2012/0203143 A1  Aug. 9, 2012

Related U.S. Application Data

(60) Provisional application No. 61/440,139, filed on Feb. 7, 2011.

(51) Int. Cl.
| | | |
|---|---|---|
| *A61N 7/02* | (2006.01) | |
| *A61B 17/32* | (2006.01) | |
| *A61B 18/14* | (2006.01) | |
| *A61B 18/00* | (2006.01) | |

(52) U.S. Cl.
CPC ..... *A61B 17/320092* (2013.01); *A61B 18/1442* (2013.01); *A61B 2018/00428* (2013.01); *A61B 2018/00607* (2013.01); *A61B 2018/00994* (2013.01); *A61B 2018/1452* (2013.01); *A61B 2018/1495* (2013.01)

(58) Field of Classification Search
CPC .............. A61N 1/06; A61N 5/00; A61N 7/00
See application file for complete search history.

(56) References Cited

U.S. PATENT DOCUMENTS

| | | | | |
|---|---|---|---|---|
| 6,773,409 | B2 * | 8/2004 | Truckai et al. | 601/2 |
| 6,821,273 | B2 * | 11/2004 | Mollenauer | 606/28 |
| 2008/0045947 | A1 * | 2/2008 | Johnson et al. | 606/51 |
| 2008/0132887 | A1 * | 6/2008 | Masuda et al. | 606/37 |

FOREIGN PATENT DOCUMENTS

| | | |
|---|---|---|
| JP | 2008-246222 | 10/2008 |
| JP | 2009-261912 | 11/2009 |

* cited by examiner

*Primary Examiner* — Theodore Stigell
*Assistant Examiner* — Natasha Patel
(74) *Attorney, Agent, or Firm* — Scully, Scott, Murphy & Presser, PC

(57) ABSTRACT

An energy treatment instrument includes an electrically conductive probe having a first electrode in a distal end portion and adapted to transmit high-frequency electric current and ultrasound vibration to the first electrode, an electrode member installed on both sides of a longitudinal axis of the first electrode separately from the electrically conductive probe and provided with a second electrode, and a movable member. The movable member is installed at a distal end of the sheath member and configured to be openable and closable with respect to the second electrode. The movable member is placed at a position facing the first electrode installed at the distal end of the probe and the second electrode and includes a third electrode provided with an electrode surface configured to be able to conduct high-frequency electric current between the third electrode and the first and second electrodes.

5 Claims, 12 Drawing Sheets

ENERGY TREATMENT INSTRUMENT

CROSS-REFERENCE TO RELATED APPLICATION

This application claims the benefit of earlier filed Provisional Application No. 61/440,139 filed on Feb. 7, 2011.

BACKGROUND OF THE INVENTION

1. Field of the Invention

The present invention relates to an energy treatment instrument, and more particularly, to an energy treatment instrument equipped with an electrically conductive probe adapted to transmit high-frequency electric current and ultrasound vibration.

2. Description of Related Art

Surgical treatment instruments are used in surgery to administer treatments such as dissection and coagulation of living tissue. Surgical treatment instruments include a so-called scissors type used to carry out treatment by pinching a living tissue. Among scissors type, energy treatment instruments which utilize ultrasound vibration, in particular, are used frequently. The reason why the energy treatment instruments which utilize ultrasound vibration are used is that the instruments allow dissection and coagulation of living tissue to be performed simultaneously, using frictional heat produced by ultrasound vibration. Especially, in removal of blood vessels, the instruments allow the removal to be carried out relying on coagulation instead of ligation or clipping, providing various advantages including simplified surgical maneuvers, reduced stress on surgeons, and reduced physical burden on patients due to shortened surgical time and/or eliminated possibility of leaving foreign bodies.

Furthermore, an energy treatment instrument equipped with an electrically conductive probe adapted to transmit high-frequency electric current and ultrasound vibration and capable of simultaneously outputting both high-frequency electric current and ultrasound vibration has been proposed as disclosed in Japanese Patent Application Laid-Open Publication No. 2009-261912. By simultaneously outputting high-frequency electric current and ultrasound vibration, the energy treatment instrument has the advantage of being able to dissect tissue faster and enable higher coagulability than conventional energy treatment instruments which utilize only ultrasound vibration. This provides merits including further reduction in surgical time, capability to coagulate and dissect thicker blood vessels, and more reliable coagulation and dissection of blood vessels without bleeding and a resulting sense of security on the part of the surgeon.

SUMMARY OF THE INVENTION

An energy treatment instrument according to one aspect of the present invention includes an electrically conductive probe having a first electrode in a distal end portion and adapted to transmit high-frequency electric current and ultrasound vibration to the first electrode; a sheath member adapted to cover at least part of the probe; an electrode member installed on both sides of a longitudinal axis of the first electrode separately from the electrically conductive probe and provided with a second electrode which extends substantially in parallel to the first electrode in a distal end direction; and a movable member installed at a distal end of the sheath member and configured to be openable and closable with respect to the first electrode and the second electrode, wherein the movable member is placed at a position facing the first electrode installed at the distal end of the probe and the second electrode and includes a third electrode provided with an electrode surface configured to be able to conduct high-frequency electric current between the third electrode and the first and second electrodes.

BRIEF DESCRIPTION OF THE DRAWINGS

FIG. 7 is a partial view of the movable jaw 31 according to the first embodiment of the present invention as viewed from below, i.e., from the side of a probe distal end portion 21a;

DETAILED DESCRIPTION OF PREFERRED EMBODIMENTS

First Embodiment (System Configuration)

Figure 1:
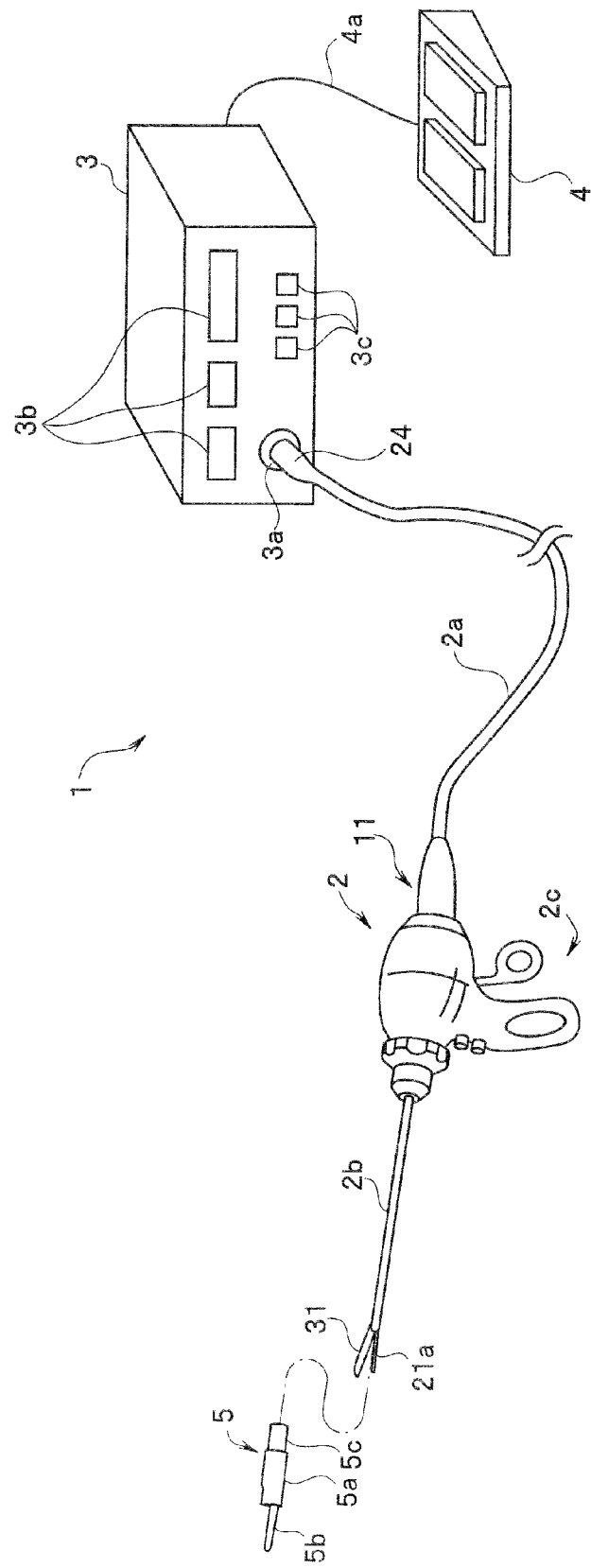
FIG. 1 is a diagram showing a surgical system according to a first embodiment of the present invention.

FIG. 1 is a diagram showing a surgical system according to a first embodiment of the present invention. The surgical system 1 which is a medical apparatus includes a handpiece 2 which is a surgical treatment instrument, a main apparatus 3 which is an output control apparatus, and a foot switch 4.

The handpiece 2 is an energy treatment instrument capable of ultrasound output and high-frequency current output. The handpiece 2 is connected to the main apparatus 3 via a detachable cable 2a. The handpiece 2 includes an insertion portion 2b, a handle unit 2c, and a transducer unit 11 and is connected to the main apparatus 3 via the cable 2a. The insertion portion 2b is configured to be detachably connectable at a distal end with a sheath member 5.

The main apparatus 3 serving as a control unit supplies at least one of a drive signal for ultrasound vibration and a drive signal for high-frequency electric current according to settings. Specifically, the main apparatus 3 has three output modes: an ultrasound output mode, a high-frequency output mode, and a simultaneous ultrasound/high-frequency output mode. The output mode is set using various operation buttons 3c or the like installed on the main apparatus 3.

The main apparatus 3 includes multiple indicators 3b and multiple various operation buttons 3c. The indicators 3b display set values and the like while the various operation buttons 3c are used to make various output settings and the like.

The foot switch 4 is connected to the main apparatus 3 via a cable 4a and adapted to output a predetermined operation signal to the main apparatus 3 when pressed by a surgeon's foot. The foot switch 4 is adapted to turn on or off ultrasound output during ultrasound output and turn on or off high-frequency output during high-frequency output. The foot switch 4 is also adapted to turn on or off simultaneous ultrasound vibration/high-frequency current output. Output values of the ultrasound and high-frequency electric current are set using operation buttons on an operation panel of the main apparatus 3.

The surgeon can perform, for example, laparoscopic surgery by holding the handpiece 2 in one hand, and another treatment instrument in the other hand.

(Overall Configuration of Handpiece)

Figure 2:
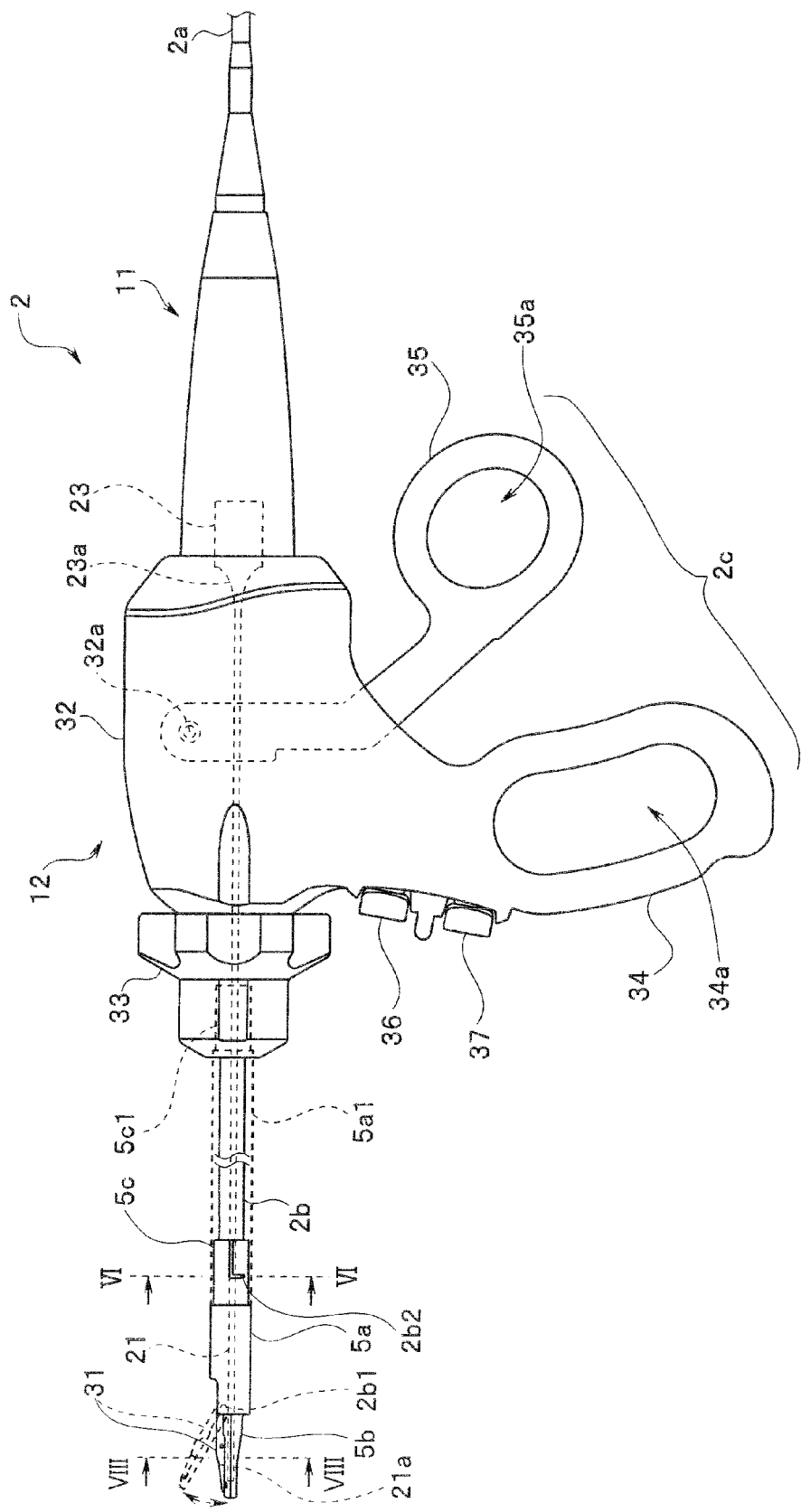
FIG. 2 is a diagram showing a configuration of a handpiece 2 according to the first embodiment of the present invention.
Figure 3:
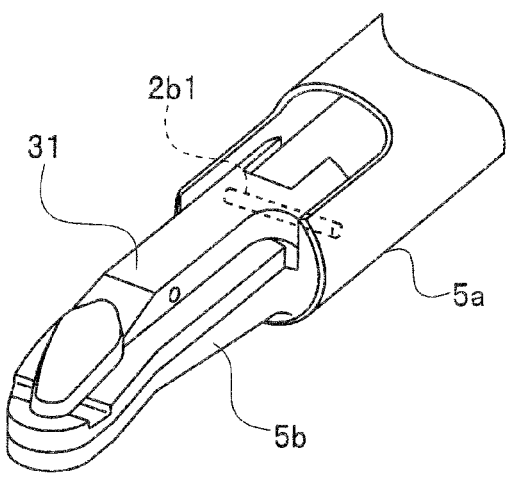
FIG. 3 is a perspective view showing a configuration of a distal end portion of the handpiece 2 according to the first embodiment of the present invention as viewed obliquely from above a distal end side of a movable jaw 31.
Figure 4:
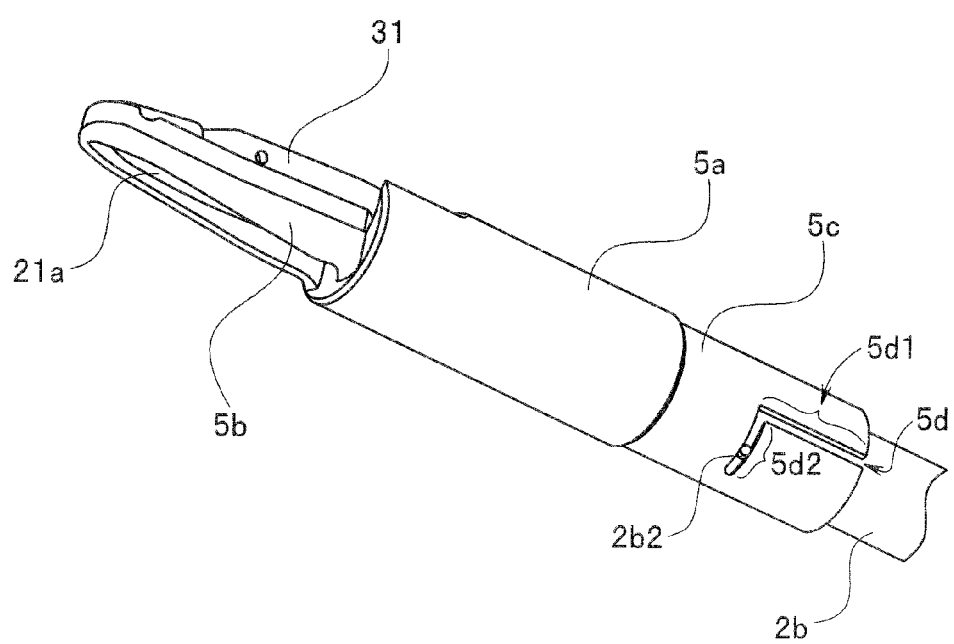
FIG. 4 is a perspective view showing the configuration of the distal end portion of the handpiece 2 according to the first embodiment of the present invention as viewed obliquely from below a distal end side of a fixed electrode 5b.

FIG. 2 is a diagram showing a configuration of the handpiece 2 according to the present embodiment. FIG. 2 is a plan view showing the configuration of the handpiece 2 according to the present embodiment. FIG. 2 shows a state in which the sheath member 5 is attached to the distal end of the insertion portion 2b. FIG. 3 is a perspective view showing a configuration of a distal end portion of the handpiece 2 as viewed obliquely from above a distal end side of a movable jaw 31. FIG. 4 is a perspective view showing the configuration of the distal end portion of the handpiece 2 as viewed obliquely from below a distal end side of a fixed electrode 5b.

As shown in FIGS. 1 and 2, the handpiece 2 includes the insertion portion 2b with a movable jaw 31 installed in a distal end portion, an operation portion body 32 installed on a proximal end side of the insertion portion 2b, the handle unit 2c installed on the operation portion body 32, and the transducer unit 11 partially placed inside the operation portion body 32 and extended from a proximal end of the operation portion body 32. An electrically conductive probe 21 capable of transmitting high-frequency electric current and ultrasound vibration is passed through the insertion portion 2b.

The cable 2a is extended from a proximal end side of the transducer unit 11. The transducer unit 11 incorporates an ultrasound transducing unit 23. The ultrasound transducing unit 23 includes multiple doughnut-shaped piezoelectric elements, a horn unit 23a adapted to amplify amplitude of vibration excited by the piezoelectric elements, and a lining plate adapted to firmly hold the piezoelectric elements and an electrode from both sides in conjunction with the horn unit 23a, where the horn unit 23a is placed on the side of the operation portion body 32 while the lining plate is located on the side of the transducer unit 11. The ultrasound transducing unit 23 is, for example, a bolt clamped Langevin ultrasound transducer unit.

The probe 21 is an electrically conductive shaft member which, being connected to the ultrasound transducing unit 23, is capable of transmitting ultrasound and high-frequency electric current. An insulating sheath (not shown) is installed, running from a distal end portion of the ultrasound transducing unit 23 to near a distal end portion of the probe 21 and covering an outer circumferential portion of the probe 21. The distal end portion 21a of the probe 21 not covered by the insulating sheath makes up an ultrasound transducing portion and high-frequency current electrode portion protruding from a distal opening of the insulating sheath (hereinafter the distal end portion of the probe 21 not covered by the insulating sheath will be referred to as the probe distal end portion 21a). The insulating sheath covers the probe 21 excluding the probe distal end portion 21a. That is, the probe 21 is an electrically conductive member equipped in the distal end portion with the probe distal end portion 21a serving as an electrode and intended to transmit high-frequency electric current and ultrasound vibration to the electrode. As shown in FIG. 1, a connector unit 24 in a proximal end portion of the cable 2a is configured to be detachable from a connector unit 3a of the main apparatus 3.

The insertion portion 2b is a tubular member made of an electrically conductive material with an outer circumferential surface covered by an insulating layer. As shown in FIGS. 2 and 3, a distal end portion is equipped with the movable jaw 31 axially and pivotably supported on a pin 2b1. The movable jaw 31 is made up of two members stacked one on top of the other. A rear end of the movable jaw 31 is connected to a drive shaft (not shown). As described later, the movable jaw 31 is configured to be openable and closable in vertical direction via the drive shaft (not shown) as indicated by dotted lines in FIG. 2 in response to operation of the handle unit 2c.

A distal end portion of the insertion portion 2b is fitted with the sheath member 5. The sheath member 5 includes a cylindrical body 5a and a fixed electrode 5b which extends from a distal end side of the cylindrical body 5a. The fixed electrode 5b is an electrode member for high-frequency electric current. A restraining portion 5c slightly smaller in outer shape is formed on a proximal end side of the cylindrical body 5a. The sheath member 5 is made of an electrically conductive material with an outer circumferential surface covered by an insulating layer. A hollow portion inside the cylindrical body 5a and restraining portion 5c is configured to allow passage of the insertion portion 2b equipped in the distal end portion with the probe 21 and the movable jaw 31.

A turning knob 33 is installed on the proximal end side of the insertion portion 2b to turn the insertion portion 2b around an axis of the insertion portion 2b. The rotation knob 33 is fixed to an outer circumference of the proximal end portion of the insertion portion 2b. On the other hand, the rotation knob 33 is rotatably coupled to the operation portion body 32 without being fixed thereto. Thus, the rotation knob 33 and the insertion portion 2b can be rotated around a longitudinal axis of the insertion portion 2b with respect to the operation portion body 32 by rotating the rotation knob 33. By turning the turning knob 33 axially around the insertion portion 2b, the surgeon can set an open and close direction of the movable jaw 31 to any desired direction.

The handle unit 2c includes a fixed handle 34 and a movable handle 35. The fixed handle 34 has been formed integrally with the operation portion body 32 and is equipped with a finger hold hole 34a which can be held by multiple fingers of the surgeon excluding the thumb. The movable handle 35 is axially and pivotably supported on a pin 32a installed on the operation portion body 32. The movable handle 35 is equipped with a finger hold hole 35a which can be held by the thumb of the surgeon.

The movable handle 35 is connected, near the pin 32a, with a proximal end portion of the drive shaft (not shown) connected to the rear end of the movable jaw 31. The handpiece 2 is configured such that the movable jaw 31 will be closed when the movable handle 35 is brought close to the fixed handle 34. That is, motion around the pin 32a of the movable handle 35 serving as a pivot center is transformed into motion around the support pin 2b1 of the movable jaw 31 serving as a pivot center. In FIG. 2, the movable jaw 31 is shown by a solid line when closed, and by a dotted line when opened.

That is, the movable jaw 31 is a movable member adapted to pinch a living tissue and installed at a distal end of the sheath member 5 in such a way as to be openable and closable with respect to the probe distal end portion 21a and the fixed electrode 5b. The movable handle 35 is an operation portion used to bring the movable jaw 31 equipped with the high-frequency current electrode close to the probe distal end portion 21a and thereby pinch the living tissue.

Also, two switch buttons 36 and 37 are installed on the operation portion body 32. The switch button 36 is a switch used to turn on and off ultrasound output and/or high-frequency current output. The switch button 37 is a switch used to change output values of ultrasound or high-frequency current. Operation signals from the switch buttons 36 and 37 of the operation portion body 32 are supplied to the main apparatus 3 via a signal line in the cable 2a.

Incidentally, the switch buttons 36 and 37 may be caused to function for high frequency output alone and the foot switch 4 may be used for ultrasound output.

Furthermore, not only the two switches on the operation portion body 32, but also the various switches 3c on the main apparatus 3 may be used to turn on and off the ultrasound output or high-frequency current output and change the output values of the ultrasound output or high-frequency current output. Besides, not only the various switches 3c on the main apparatus 3, but also the two switches on the operation portion body 32 may be used to set the output mode and the like.

As described above, the distal end portion of the probe 21, the movable jaw 31, and the fixed electrode 5b make up a scissors type hold unit in the distal end portion of the insertion portion 2b. Regardless of whether the sheath member 5 is attached or not, the handpiece 2 is capable of producing three types of output: ultrasound output, high-frequency output, and simultaneous ultrasound/high-frequency output.

Although in FIGS. 1 and 2, the sheath member 5 is fitted over the distal end portion of the insertion portion 2b and structured to cover a distal end of the insertion portion 2b and part in the neighborhood thereof, as a variation of the sheath member 5, a cylindrical body 5a1 may be extended to also cover the proximal end portion of the insertion portion 2b (i.e., a distal end side of the operation portion body 32) as indicated by dotted lines in FIG. 2. In that case, a restraining portion 5c1 is located in the turning knob 33 for may be located in the operation portion body 32).

(Configuration of Distal End Portion of Handpiece 2)

Next, a configuration of the distal end portion of the handpiece 2 will be described.

Figure 5:
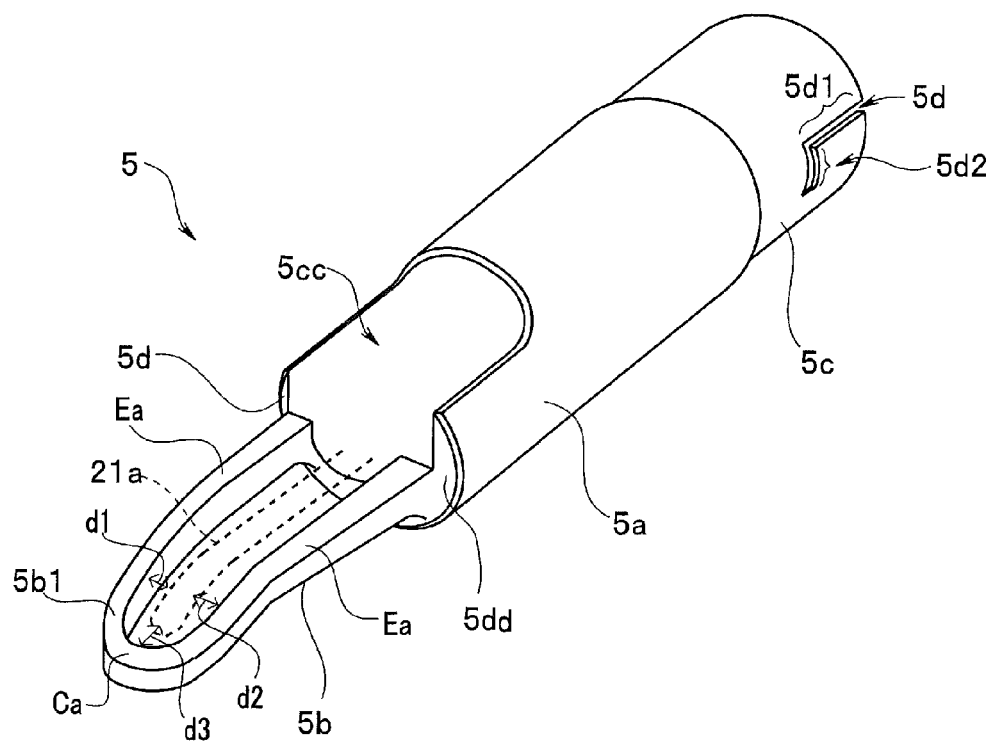
FIG. 5 is a perspective view showing a configuration of a distal end portion of a sheath member 5 according to the first embodiment of the present invention.

First, a configuration of the sheath member 5 will be described. FIG. 5 is a perspective view showing a configuration of a distal end portion of the sheath member 5. The sheath member 5 has a notched portion 5cc formed in part of a distal end portion of the cylindrical body 5a to cover at least part of the probe 21. The notched portion 5cc also functions as an opening portion which allows the movable jaw 31 to open and close when the sheath member 5 is fitted over the distal end of the insertion portion 2b.

An inward flange portion 5dd is installed in part of the distal end portion of the cylindrical body 5a. Because of the notched portion 5cc, the inward flange portion 5dd is arc-shaped when the insertion portion 2b is viewed from the distal end side. When the sheath member 5 is fitted over the distal end of the insertion portion 2b, the distal end portion of the insertion portion 2b abuts the inward flange portion 5dd, defining a positional relationship among the probe distal end portion 21a, the movable jaw 31, and the fixed electrode 5b.

The fixed electrode 5b is installed in the distal end portion of the sheath member 5 and has a U-shape which extends in a distal end direction from the cylindrical body 5a. The fixed electrode 5b has a surface 5b1 which faces the movable jaw 31. The U-shape of the fixed electrode 5b is bent in the distal end direction of the cylindrical body 5a by a predetermined angle with respect to an axial direction of the cylindrical body 5a. That is, on the distal end side, the U-shape is somewhat bent in the distal end direction of the fixed electrode 5b.

Also, the fixed electrode 5b has enough rigidity not to deflect even if subjected to a pressing force of the movable jaw 31. In this case, the fixed electrode 5b is made of, for example, stainless steel and does not deflect more than 0.1 mm even if subjected to a pressing force of the movable jaw 31.

The fixed electrode 5b has two extension portions Ea placed on both sides of the probe distal end portion 21a and extended in the distal end direction of the probe distal end portion 21a when the sheath member 5 is fitted over the insertion portion 2b. The two extension portions Ea prevent the probe distal end portion 21a heated to high temperatures by ultrasound vibration from inadvertently coming into direct contact with surrounding living tissues.

The distal ends of the two extension portions Ea are coupled via a coupling unit Ca. Since the two extension portions Ea are coupled to each other in respective distal end portions via the coupling unit Ca, the extension portions Ea and the coupling unit Ca form the U-shape of the fixed electrode 5b.

When the sheath member 5 is fitted over the insertion portion 2b, gaps d1, d2, and d3 are formed, respectively, between the probe distal end portion 21a and the two extension portions Ea and between the probe distal end portion 21a and the coupling unit Ca.

As described above, the fixed electrode 5b is an electrode member installed, separately from the probe 21, on both sides of a longitudinal axis of the probe distal end portion 21a, extending in the distal end direction substantially in parallel to the probe distal end portion 21a which is an electrode.

To fit the sheath member 5 detachably over the probe 21, a slit 5d is formed on the proximal end side in the restraining portion 5c of the cylindrical body 5a. The slit 5d has an axial direction part 5d1 formed along the axial direction of the cylindrical body 5a and a circumferential direction part 5d2 formed along a circumferential direction, making up a fitting unit used to fit the sheath member 5 detachably over the probe 21.

As shown in FIGS. 2 and 4, a pin 2b2 is installed on the insertion portion 2b, protruding radially outward. The pin 2b2 is made of an electrically conductive metal and screwed or press-fitted at one end into the probe 21. An outer circumferential surface of the pin 2b2 comes into contact with an inner wall surface of the slit 5d in the restraining portion 5c, and an active line for high-frequency electric current is electrically connected to the fixed electrode 5b via the pin 2b2 and the cylindrical body 5a. A recovery line for the high-frequency electric current is connected to the movable jaw 31.

To fit the sheath member 5 over the distal end portion of the insertion portion 2b, first the surgeon inserts the distal end portion of the insertion portion 2b into the sheath member 5 through an opening on the proximal end side of the restraining portion 5c and abuts the distal end portion of the insertion portion 2b against the inward flange portion 5dd. In so doing, the insertion portion 2b is inserted through the opening on the proximal end side of the restraining portion 5c by passing the pin 2b2 through the axial direction part 5d1 of the slit 5d and after the pin 2b2 abuts the circumferential direction part 5d2, the sheath member 5 can be fitted over the distal end portion of the insertion portion 2b by turning the insertion portion 2b in a circumferential direction of the restraining portion 5c.

The pin 2b2 is installed at a node position where there is no vibration so as to eliminate the problems of unusual noise, heat generation, and the like even if the probe 2b comes into contact with the pin 2b2 when the probe 2b performs ultrasound vibration. This is because when the probe 2b performs ultrasound vibration, part located at the node position does not move even if stress is applied. That is, when the sheath member 5 is fitted over the probe 2b, the slit 5d serving as a fitting unit comes into contact with the pin 2b2 installed at the node position of the ultrasound vibration performed by the probe 2b and thereby supplies high-frequency electric current from the probe 2b to the fixed electrode 5b.

Figure 6:
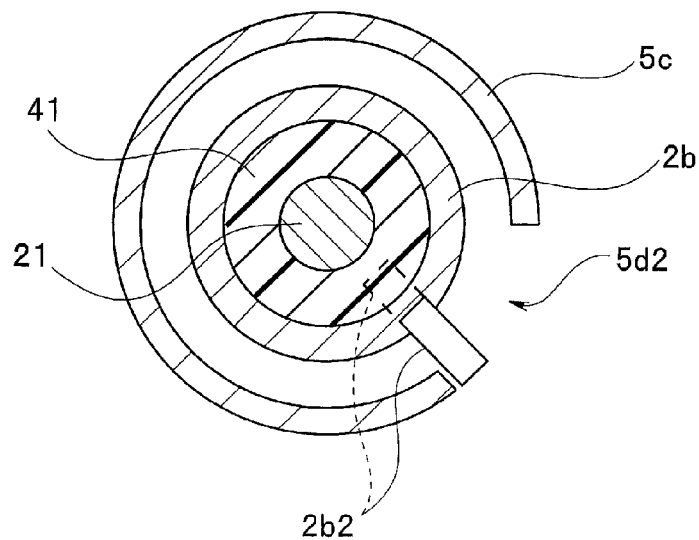
FIG. 6 is a sectional view taken along line VI-VI in FIG. 2.

Incidentally, the pin 2b2 may be installed on a member other than the probe 21. FIG. 6 is a diagram for illustrating a situation in which the pin 2b2 is installed on a member other than the probe 21. FIG. 6 is a sectional view taken along line VI-VI in FIG. 2. Incidentally, in FIG. 6, insulating layers installed on an outer circumferential side of the sheath member 5 and the probe 2b are omitted.

In FIG. 6, the probe 21 is partially covered by an electrically conductive lining 41. The pin 2b2 is electrically connected by being screwed or press-fitted into the insertion portion 2b placed in contact with the electrically conductive lining 41. Again, the pin 2b2 is installed at the node position of the ultrasound vibration performed by the probe 2b. That is, the high-frequency electric current from the probe 2b is supplied to the fixed electrode 5b via the electrically conductive lining installed on an outer circumference of the probe 2b.

Alternatively, as indicated by dotted lines in FIG. 6, the pin 2b2 may be screwed or press-fitted into the electrically conductive lining 41 covering the probe 21. In that case, again, the probe 21 and the pin 2b2 are electrically connected with each other via the electrically conductive lining 41.

Figure 7:
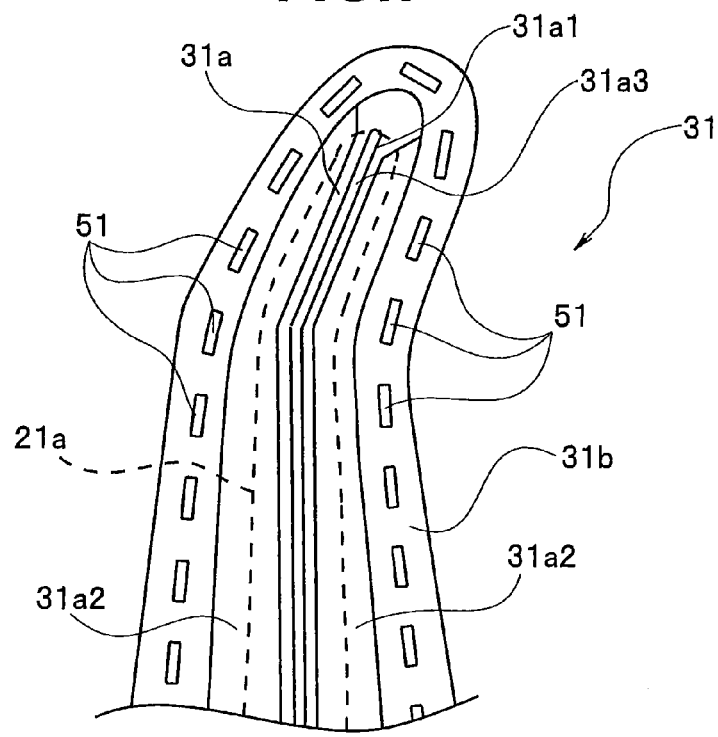

FIG. 7 is a partial view of the movable jaw 31 as viewed from below, i.e., from the side of the probe distal end portion 21a. On the side of the probe distal end portion 21a, the movable jaw 31 has the Teflon pad 31a which is an insulative pad member adapted to abut the probe distal end portion 21a, and a surface 31b configured to face the surface 5b1 of the fixed electrode 5b. A stepped portion 31a1 configured to follow shape of the probe distal end portion 21a is formed on that part of the Teflon pad 31a which comes into contact with the probe distal end portion 21a. Inclined surfaces 31a2 are formed between an edge of an end portion of the Teflon pad 31a and the surface 31b (see FIG. 9).

Figure 9:
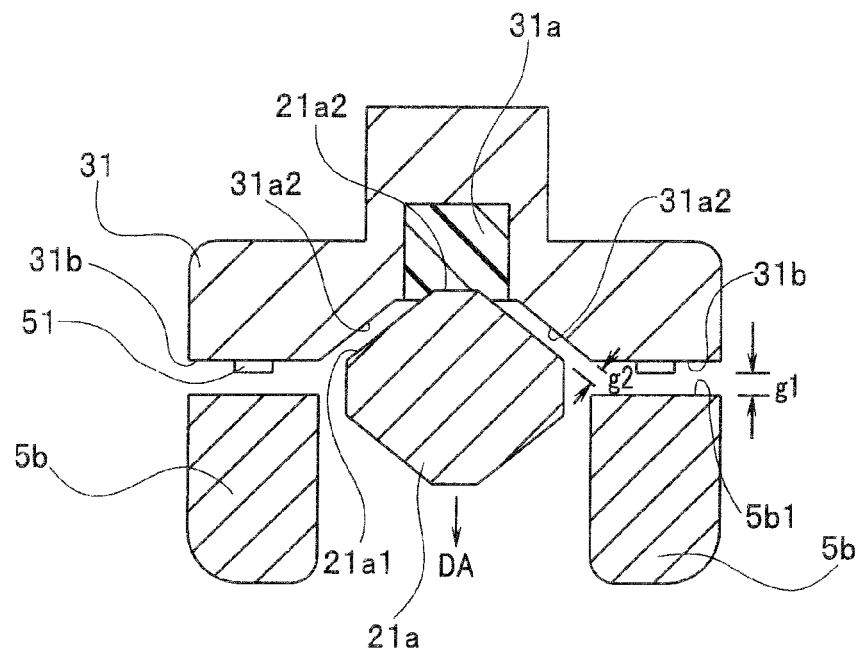
FIG. 9 is a diagram for illustrating a state brought about when the movable jaw 31 comes into contact with the probe distal end portion 21a as a movable handle 35 is operated so as to come close to a fixed handle 34.
Figure 10:
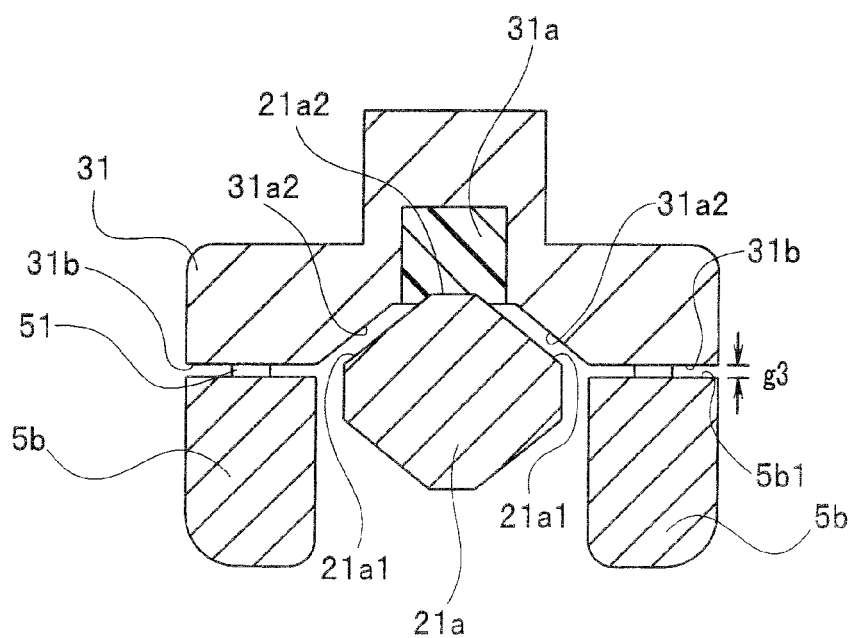
FIG. 10 is a diagram for illustrating a state brought about when multiple insulating members 51 of the movable jaw 31 come into contact with a surface 5b1 of the fixed electrode 5b as the movable handle 35 is operated so as to come close to the fixed handle 34.

Also, the probe distal end portion 21a includes a planar, ultrasound processing surface 21a2 adapted to abut the Teflon pad 31a and high-frequency current processing surfaces 21a1 formed on both sides of the ultrasound processing surface and provided with inclined surfaces 31a (see FIGS. 9 and 10). That is, the movable jaw 31 has the Teflon pad 31a at a position facing the probe distal end portion 21a and has a high-frequency current electrode installed on both sides of the Teflon pad 31a.

Also, multiple insulating members 51 made of ceramic or the like which has heat resistance are installed on the surface 31b. The multiple insulating members 51 are provided to prevent electrical short-circuits between the movable jaw 31 and the fixed electrode 5b during high-frequency output.

As described above, the movable jaw 31 is placed at a position facing the probe distal end portion 21a provided at a distal end of the probe 21 as well as facing the fixed electrode 5b. Besides, the movable jaw 31 includes a third electrode equipped with an electrode surface capable of transmitting high-frequency electric current between the probe distal end portion 21a which is a first electrode and the fixed electrode 5b which has a second electrode.

(Grasping Forces in Distal End Portion of Handpiece 2)

Next, contact forces among the movable jaw 31, probe distal end portion 21a, and fixed electrode 5b which make up the distal end portion of the handpiece 2 will be described.

Figure 8:
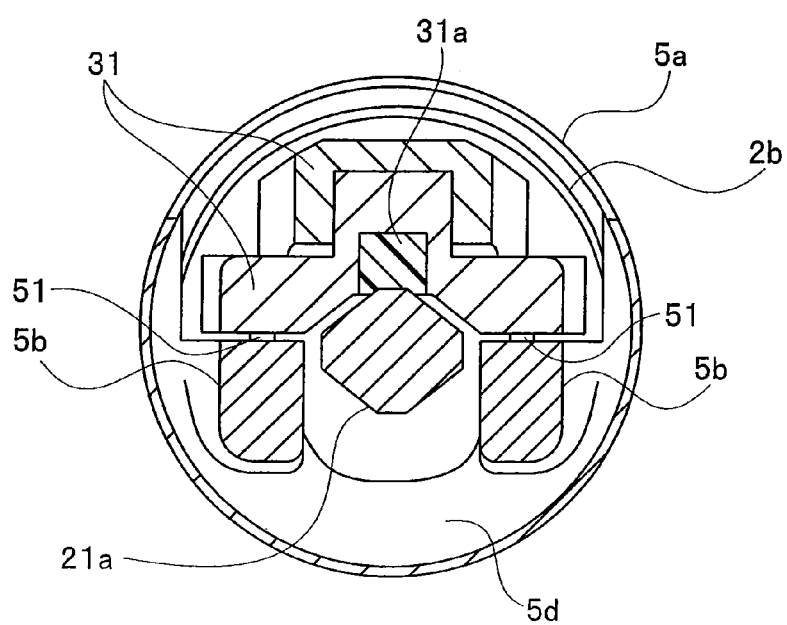
FIG. 8 is a sectional view of the distal end portion of the handpiece 2 taken along line VIII-VIII in FIG. 2, with the movable jaw 31 and the fixed electrode 5b closed.
Figure 11:
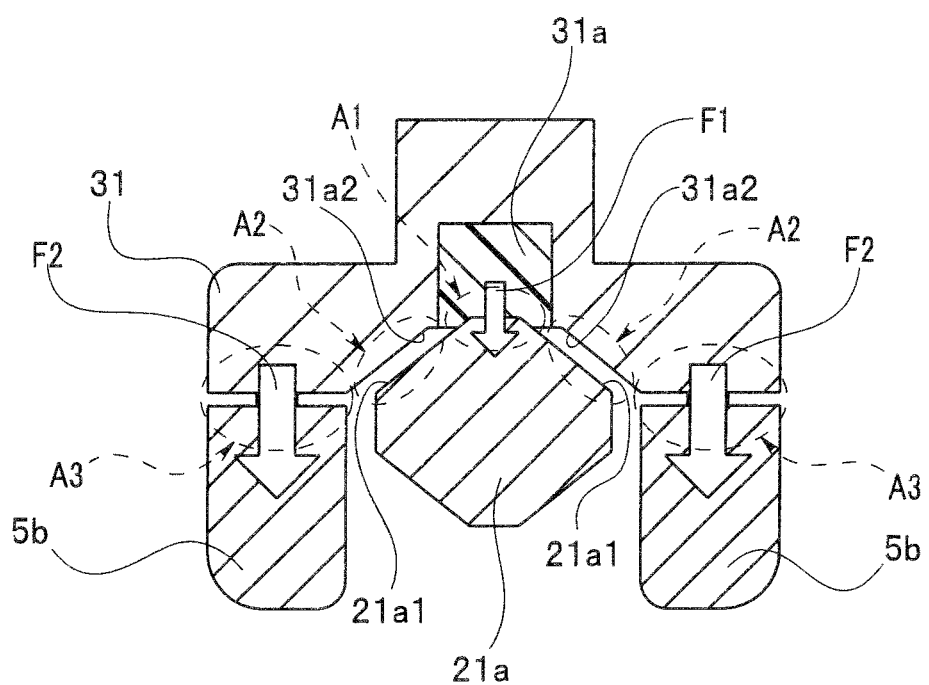
FIG. 11 is a diagram for illustrating a relationship between a contact force F1 and a contact force F2 when a living tissue is grasped between the movable jaw 31 and the probe distal end portion 21a, where the contact force F1 acts between a Teflon pad 31a and the probe distal end portion 21a while the contact force F2 acts between the multiple insulating members 51 and the surface 5b1 of the fixed electrode 5b.

FIG. 8 is a sectional view of the distal end portion of the handpiece 2 taken along line VIII-VIII in FIG. 2, with the movable jaw 31 and the fixed electrode 5b closed. FIGS. 9 to 11 are diagrams for illustrating grasping forces in the distal end portion of the handpiece 2. FIG. 9 is a diagram for illustrating a state brought about when the movable jaw 31 comes into contact with the probe distal end portion 21a as the movable handle 35 is operated so as to come close to the fixed handle 34.

As shown in FIG. 9, when the probe distal end portion 21a comes into contact with the Teflon pad 31a of the movable jaw 31 with the movable handle 35 being operated by the surgeon so as to come close to the fixed handle 34, the probe distal end portion 21a, which is not yet subjected to a force from the movable jaw 31, is not deflected. At this point, the multiple insulating members 51 are a predetermined distance g1 away from the surface 5b1 of the fixed electrode 5b.

Subsequently, as the Teflon pad 31a of the movable jaw 31 pushes down the probe distal end portion 21a in response to operation of the movable handle 35, the probe distal end portion 21a begins to deflect in a direction indicated by arrow DA.

As the surgeon continues to operate the movable handle 35 further, the multiple insulating members 51 installed on the surface 31b of the movable jaw 31 come into contact with the surface 5b1 of the fixed electrode 5b. FIG. 10 is a diagram for illustrating a state brought about when the multiple insulating members 51 of the movable jaw 31 come into contact with the surface 5b1 of the fixed electrode 5b as the movable handle 35 is operated so as to come close to the fixed handle 34. When the multiple insulating members 51 come into contact with the surface 5b1 of the fixed electrode 5b, the surface 31b and the surface 5b1 are a predetermined distance g3 away from each other.

After the multiple insulating members 51 come into contact with the surface 5b1 of the fixed electrode 5b, even if the surgeon continues to operate the movable handle 35, the fixed electrode 5b, which has high rigidity, does not deflect.

That is, once the multiple insulating members 51 come into contact with the surface 5b1 of the fixed electrode 5b, even if the surgeon continues to operate the movable handle 35, since the fixed electrode 5b does not deflect, the probe distal end portion 21a does not deflect more than a predetermined amount of deflection.

When the movable jaw 31 is closed with respect to the fixed electrode 5b as shown in FIG. 10, the probe distal end portion 21a is placed in contact with the Teflon pad 31a of the movable jaw 31 while the multiple insulating members 51 are placed in contact with the surface 5b1 of the fixed electrode 5b.

With the living tissue pinched between the movable jaw 31 and the probe distal end portion 21a and with the multiple insulating members 51 placed in contact with the surface 5b1 of the fixed electrode 5b, when the surgeon presses the foot switch 4 for simultaneous ultrasound vibration/high-frequency current output with a foot, between the movable jaw 31 and the probe distal end portion 21a, high-frequency electric current and ultrasound vibration are applied to the living tissue which is a treatment site while high-frequency electric current is applied between the movable jaw 31 and the fixed electrode 5b as well as between the movable jaw 31 and the probe distal end portion 21a.

Specifically, the probe distal end portion 21a has an octagonal cross-sectional shape. When the movable jaw 31 is closed with respect to the fixed electrode 5b, one surface 21a2 facing toward the movable jaw 31 in the probe distal end portion 21a is placed in contact with the stepped portion 31a1 of the movable jaw 31. Consequently, the treatment site, i.e., the living tissue pinched between the probe distal end portion 21a and the contact surface of the movable jaw 31 is supplied with both ultrasound vibration and high-frequency electric current for treatment.

Also, when the movable jaw 31 is closed with respect to the fixed electrode 5b, the multiple insulating members 51 installed on the surface 31b of the movable jaw 31 are placed in contact with the surface 5b1 of the fixed electrode 5b. Furthermore, when the movable jaw 31 is closed with respect to the fixed electrode 5b, the two inclined surfaces 31a2 of the movable jaw 31 oppose the two respective surfaces 21a1 of the probe distal end portion 21a, being separated from the two surfaces 21a1 by a predetermined distance g2. That is, the two inclined surfaces 31a2 and the two surfaces 21a1 are placed in opposing positional relationship with each other.

Between the Teflon pad 31a of the movable jaw 31 and the surfaces 21a2 of the probe distal end portion 21a, the living tissue is treated by the application of ultrasound vibration. Furthermore, between the surface 31b of the movable jaw 31 and the surface 5b1 of the fixed electrode 5b as well as between the two inclined surfaces 31a2 of the movable jaw 31 and the two inclined surfaces 21a1 of the probe distal end portion 21a, the living tissue is supplied with high-frequency electric current for treatment.

Now, the contact force between the movable jaw 31 and the probe distal end portion 21a as well as the contact force between the movable jaw 31 and the fixed electrode 5b will be described. As the surgeon brings the movable handle 35 close to the fixed handle 34 by operating the movable handle 35, the Teflon pad 31a of the movable jaw 31 comes into contact with the probe distal end portion 21a first. As the surgeon continues to operate the movable handle 35 after the contact, the probe distal end portion 21a begins to deflect under the pressing force from the movable jaw 31.

In other words, the fixed electrode 5b is placed relative to the probe distal end portion 21a such that when the movable jaw 31 becomes closed with respect to the probe distal end portion 21a and the fixed electrode 5b, the probe distal end portion 21a and the Teflon pad 31a will come into contact with each other before the fixed electrode 5b and the insulating members 51 come into contact with each other.

Therefore, after the Teflon pad 31a of the movable jaw 31 comes into contact with the probe distal end portion 21a, the contact forces F1 and F2 can be adjusted by adjusting a distance between the fixed electrode 5b and the multiple insulating members 51 with the probe distal end portion 21a deflecting until the multiple insulating members 51 come into contact with the surface 5b1 of the fixed electrode 5b.

FIG. 11 is a diagram for illustrating a relationship between the contact force F1 and the contact force F2 when a living tissue is grasped between the movable jaw 31 and the probe distal end portion 21a, where the contact force F1 acts between the Teflon pad 31a and the probe distal end portion 21a while the contact force F2 acts between the multiple insulating members 51 and the surface 5b1 of the fixed electrode 5b.

As shown in FIG. 11, when the surgeon closes the movable jaw 31 with respect to the fixed electrode 5b to pinch the living tissue by operating the movable handle 35, the contact force F1 between the Teflon pad 31a of the movable jaw 31 and the probe distal end portion 21a is smaller than the contact force F2 between the multiple insulating members 51 and the surface 5b1 of the fixed electrode 5b. This is because as shown in FIGS. 9 and 10, the fixed electrode 5b is disposed relative to the probe distal end portion 21a so as to define the positional relationship among the movable jaw 31, the probe distal end portion 21a, and the fixed electrode 5b such that when the movable handle 35 is operated, the Teflon pad 31a and the probe distal end portion 21a come into contact with each other before the multiple insulating members 51 and the fixed electrode 5b come into contact with each other.

In other words, by adjusting the positional relationship among the movable jaw 31, the probe distal end portion 21a, and the fixed electrode 5b, it is possible to adjust and set the two contact forces to desired values. For example, the contact force F1 can be set to 10 N (newtons) and the contact force F2 can be set to 30 N (newtons).

That is, the fixed electrode 5b is placed relative to the probe distal end portion 21a such that when the movable jaw 31 is closed with respect to the probe distal end portion 21a and the fixed electrode 5b, the probe distal end portion 21a and the Teflon pad 31a will be placed in contact with each other and that when the insulating members 51 installed on the movable jaw 31 are placed in contact with the fixed electrode 5b as well, the grasping force F2 in a contact area between the insulating members 51 and fixed electrode 5b will be larger than the grasping force F1 in a contact area between the probe distal end portion 21a and the Teflon pad 31a.

When a blood vessel is coagulated and dissected using the handpiece 2 of this configuration, that part of the blood vessel which is located in a first treatment area A1 indicated by a dotted line in FIG. 11 undergoes coagulation and dissection treatment under ultrasound vibration while being pressed by the contact force F1. That part of the blood vessel which is located in second treatment areas A2 indicated by dotted lines undergoes coagulation treatment under ultrasound vibration and high-frequency electric current by being pinched between the inclined surfaces 31a2 of the movable jaw 31 and the surfaces 21a1 of the probe distal end portion 21a. Furthermore, that part of the blood vessel which is located in third treatment areas A3 indicated by dotted lines undergoes coagulation treatment under high-frequency electric current while being pressed by the contact force F2.

Therefore, two sealed regions—one sealed in the second treatment areas and the other sealed in the third treatment areas—are formed around a cutting site of the blood vessel by a single grip operation of the operation portion. When the second treatment areas and the third treatment areas are compared, the third treatment areas have higher blood vessel sealing performance than do the second treatment areas.

Figure 12:
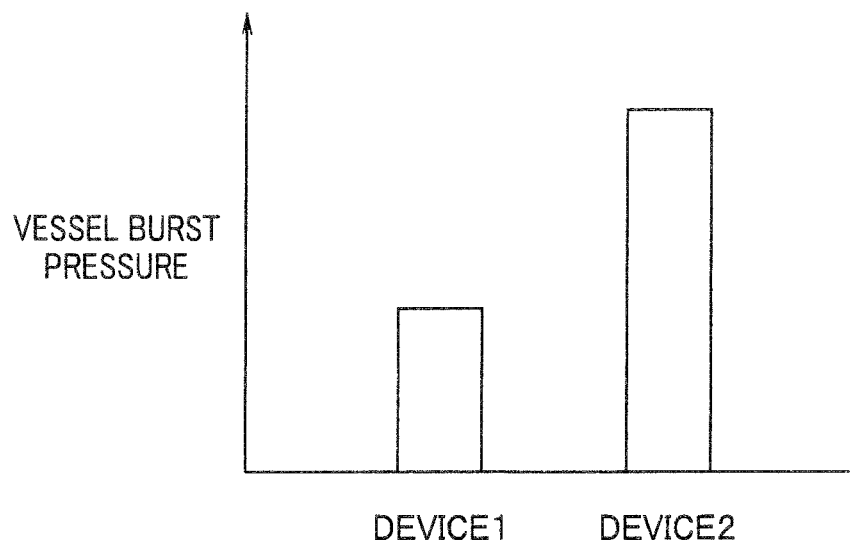
FIG. 12 is a graph showing vessel burst pressure of a handpiece without a fixed electrode and vessel burst pressure of a handpiece with a fixed electrode.

FIG. 12 is a graph showing vessel burst pressure of a handpiece without a fixed electrode and vessel burst pressure of a handpiece with a fixed electrode. The present applicant experimentally measured vessel burst pressures of a handpiece without a fixed electrode and the handpiece 2 with the fixed electrode 5b under predetermined conditions. FIG. 12 shows results of the experiment.

In FIG. 12, device 1 (DEVICE1) is the handpiece without a fixed electrode and device 2 (DEVICE2) is the handpiece 2 with the fixed electrode 5b. As shown in FIG. 12, the vessel burst pressure of the handpiece 2 with the fixed electrode 5b was higher than the vessel burst pressure of the handpiece without a fixed electrode.

That is, the above-described handpiece 2, which is provided with the fixed electrode 5b and is able to increase the contact force F2 between the insulating members 51 of the movable jaw 31 and the surface 5b1 of the fixed electrode 5b, can achieve higher sealing performance than the sealing performance of the handpiece without a fixed electrode.

Furthermore, since the two contact forces F1 and F2 can be adjusted and set to desired values by adjusting the positional relationship among the movable jaw 31, the probe distal end portion 21a, and the fixed electrode 5b, oscillation efficiency during ultrasound vibration was also higher than the oscillation efficiency of the handpiece without a fixed electrode.

The oscillation efficiency represents the limits to which the probe distal end portion 21a can vibrate. A high oscillation efficiency of ultrasound vibration means that even a hard living tissue such as the stomach, the small intestine, and the uterus ligaments, harder than, for example, blood vessels can be treated. That is, the handpiece 2 was able to improve load resistance to ultrasound vibration.

Figure 13:
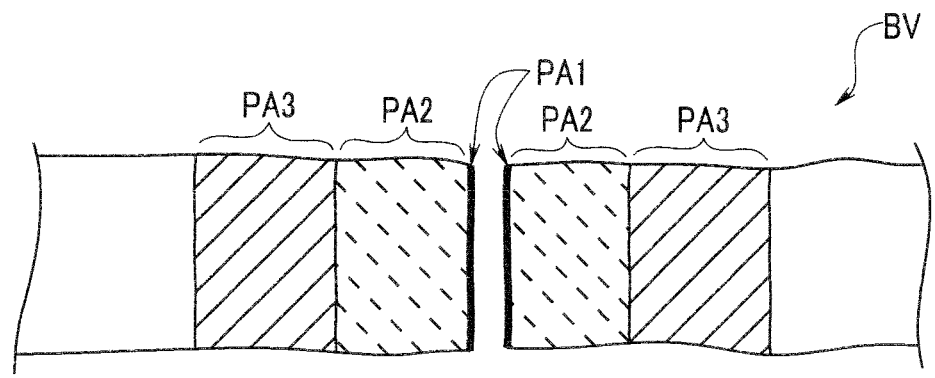
FIG. 13 is a diagram for illustrating a state of a blood vessel dissected using the handpiece 2 according to the first embodiment of the present invention.

FIG. 13 is a diagram for illustrating a state of a blood vessel dissected using the handpiece 2 according to the present embodiment.

An end portion PA1 of the blood vessel in the treatment area A1 has been coagulated, cut, and sealed. The end portion PA1 and a surrounding area thereof have coagulated strongly.

Areas PA2 of the blood vessel in the treatment areas A2 have coagulated in a gap g2 between the surfaces 31a2 and 21a1 with a predetermined interval.

Areas PA3 of the blood vessel in the treatment areas A3 have coagulated by being pressed with the larger contact force F2, and thus coagulated more strongly than in the areas PA2.

Surface color of the blood vessel in the treatment areas PA3 coagulated strongly is different from surface color of the blood vessel in the treatment areas PA2. Consequently, the areas PA3 appear strip-shaped, allowing the surgeon to verify after dissection that the strip-shaped part has coagulated reliably.

(Advantages)

Therefore, when a blood vessel is dissected by simultaneously outputting ultrasound vibration and high-frequency electric current, the handpiece according to the present embodiment delivers high blood vessel sealing performance and makes it easy for the surgeon to visually check that surroundings of the dissection site have coagulated reliably.

Thus, the use of the handpiece 2 eliminates the need for the surgeon to carry out coagulation on both sides of a dissection site using high-frequency electric current before conducting dissection treatment, unlike conventional procedures, and thereby makes it possible to reduce surgical time.

Furthermore, the above-described capability to adjust the contact forces F1 and F2 has the following merits.

Basically, there is a problem in that if the probe distal end portion 21a deflects too much, cracks could develop in the probe distal end portion 21a itself. The development of cracks in the probe distal end portion 21a can result in a rupture of the probe itself or a loss of parts. However, the configuration described above can keep the probe distal end portion 21a from deflecting more than a predetermined amount of deflection and thereby prevent the occurrence of such problems.

Also, by adjusting the contact forces F1 and F2 as described above, it is possible to deal with the problems of the vibration load resistance of the probe distal end portion 21a to ultrasound vibration and wear resistance of the Teflon pad 31a.

Furthermore, by adjusting the contact forces F1 and F2 as described above, it is possible to deal with the problem of slippage caused by ultrasound vibration when a living tissue is grasped.

Also, the use of the handpiece 2 described above has the merit of being able to treat an extended area: for example, even part of the stomach, the small intestine, or the like can be removed by means of strong coagulation. Specifically, both the movable jaw 31 and fixed electrode 5b have the shape of letter U pointing toward the distal end.

Therefore, part of the stomach or the like can be removed without producing a hole in the stomach or other organ.

Figure 14:
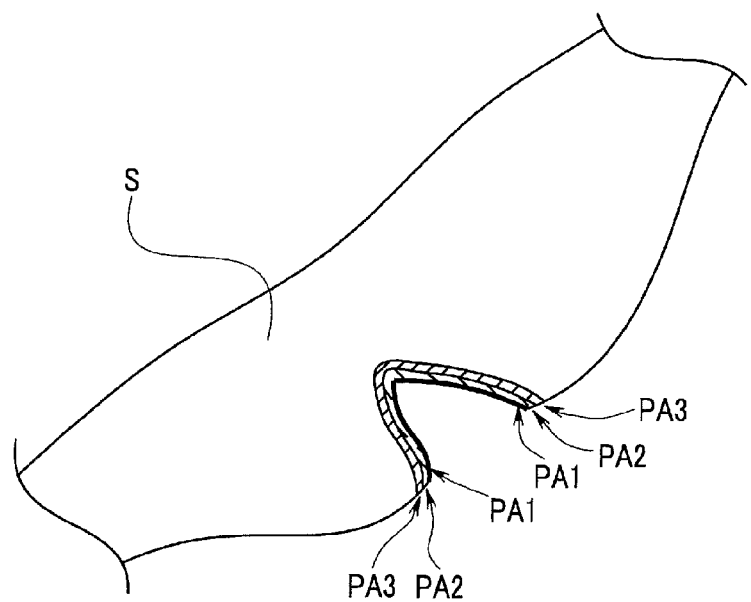
FIG. 14 is a diagram for illustrating a state which results when part of an organ such as the stomach is removed.

FIG. 14 is a diagram for illustrating a state which results when part of an organ such as the stomach is removed. The distal end portion of the handpiece 2 is a U-shaped hold unit. Furthermore, the surface 31b of the movable jaw 31 and the surface 5b1 of the fixed electrode 5h have U-shapes substantially similar to each other.

Thus, when part of an organ S is removed as shown in FIG. 14, since the living tissue is treated by high-frequency electric current by being pinched with a large contact force even in a distal end portion of the U-shape, the part can be removed without producing a hole in the organ S.

To conduct a treatment such as shown in FIG. 14, first the surgeon removes or coagulates the mesentery, blood vessels, and the like using the handpiece 2 without the sheath member 5 fitted over the probe 2b.

Subsequently, the surgeon pulls the handpiece 2 out of a trocar passed through a body wall of a subject, fits the sheath member 5 over the distal end of the insertion portion 2b, inserts the handpiece 2 into the trocar again, and can conduct a treatment such as shown in FIG. 14 using the handpiece 2 fitted with the sheath member 5. This has the merit that the surgeon can carry out treatment of a relatively large organ quickly using the above-described handpiece 2.

As described above, when a living tissue is coagulated and dissected simultaneously by simultaneously outputting high-frequency electric current and ultrasound vibration, the handpiece 2 according to the present embodiment delivers high sealing performance and makes it easy to visually check that surroundings of the dissection site have coagulated reliably.

(Variations)

Next, variations will be described. Although variations of the present embodiment have been mentioned in the above description, further variations will be described below.

Figure 15:
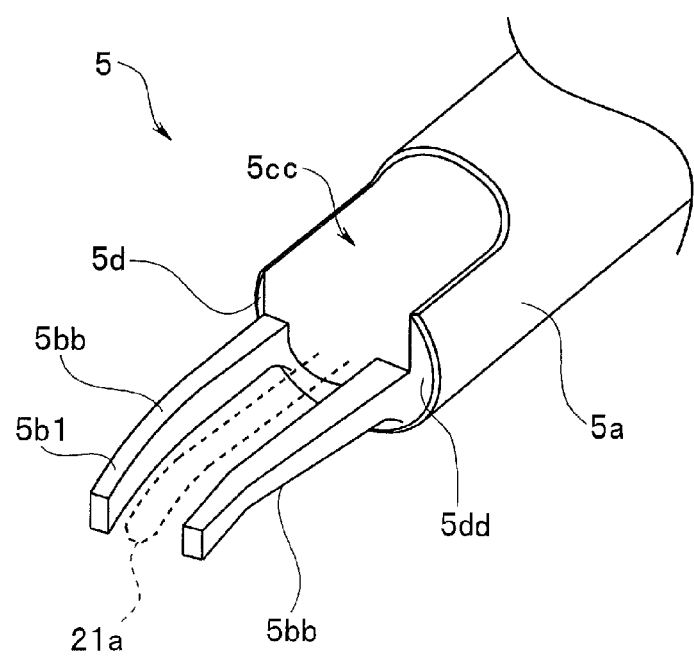
FIG. 15 is a perspective view of a fixed electrode 5bb which is a variation of the fixed electrode 5b.

FIG. 15 is a perspective view of a fixed electrode 5bb which is a variation of the fixed electrode 5b. As shown in FIG. 15, the fixed electrode 5bb may be an electrode member made up of two arms extending toward the distal end. That is, whereas both the movable jaw 31 and the fixed electrode 5b are U-shaped in the embodiment described above, in FIG. 15, the fixed electrode 5bb is made up of two arms whose distal end portions are not connected.

This configuration also provides advantages similar to the advantages of the embodiment described above.

Figure 16:
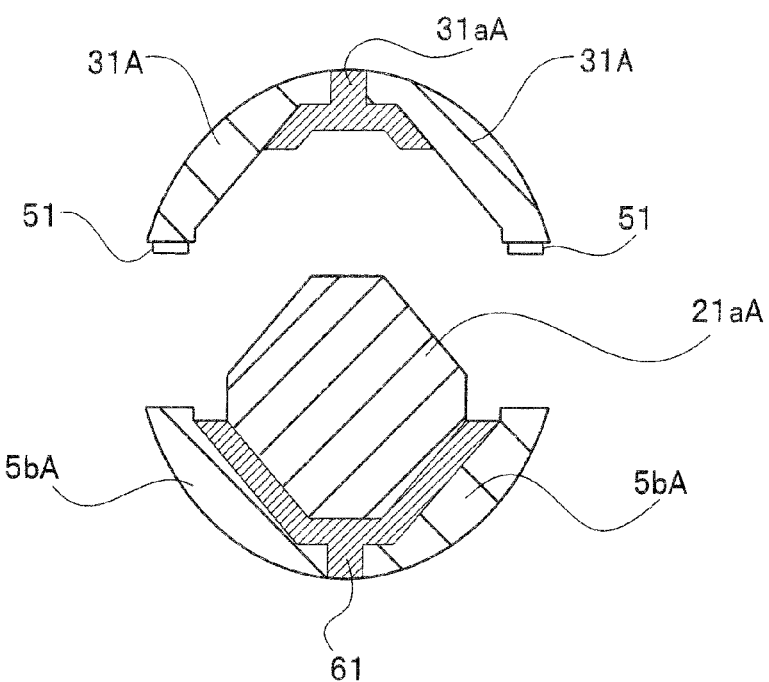
FIG. 16 is a sectional view of a variation of the movable jaw and fixed electrode of the handpiece 2.

FIG. 16 is a sectional view of a variation of the movable jaw 31 and fixed electrode of the handpiece 2. FIG. 16 is a sectional view taken along line XIII-XIII in FIG. 2.

When compared to FIG. 8, a movable jaw 31A in FIG. 16 is circular in cross-sectional shape on an outer circumferential side and a Teflon pad 31aA also differs in cross-sectional shape. Furthermore, a fixed electrode 5bA is installed under a probe distal end portion 21aA via an insulating member 61. The fixed electrode 5bA and the probe distal end portion 21aA are integrated with each other. The fixed electrode 5bA is also circular in cross-sectional shape on an outer circumferential side. When the movable jaw 31A is closed with respect to the fixed electrode 5bA, if the Teflon pad 31aA and the probe distal end portion 21aA come into contact with each other, the insulating members 51 and a surface 5b1 of the fixed electrode 5bA come into contact with each other at the same time.

This configuration also provides advantages similar to the advantages of the embodiment described above.

Figure 17:
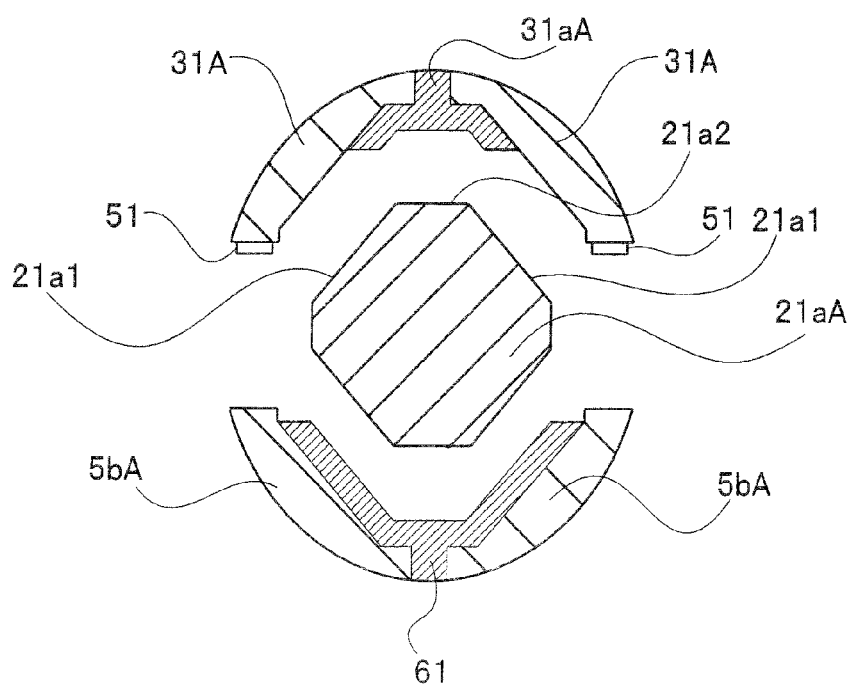
FIG. 17 is a sectional view of a variation of the movable jaw and fixed electrode of the handpiece 2 when a probe distal end portion 21aA and a fixed electrode 5bA are not integrated with each other.

Furthermore, as a variation of FIG. 16, the probe distal end portion 21aA and the fixed electrode 5bA does not need to be integrated with each other. FIG. 17 is a sectional view of a variation of the movable jaw and fixed electrode of the handpiece 2 when the probe distal end portion 21aA and the fixed electrode 5bA are not integrated with each other.

In FIG. 17, the probe distal end portion 21aA and the fixed electrode 5bA are separated and disposed such that when the movable jaw 31A is closed with respect to the fixed electrode 5bA, the Teflon pad 31aA and a surface 21a2 of the probe distal end portion 21aA come into contact with each other before the insulating members 51 and a surface 5b1 of the fixed electrode 5bA come into contact with each other. Thus, the handpiece 2 of the configuration in FIG. 17 can achieve the same operation and advantages as those described in FIG. 11.

Figure 18:
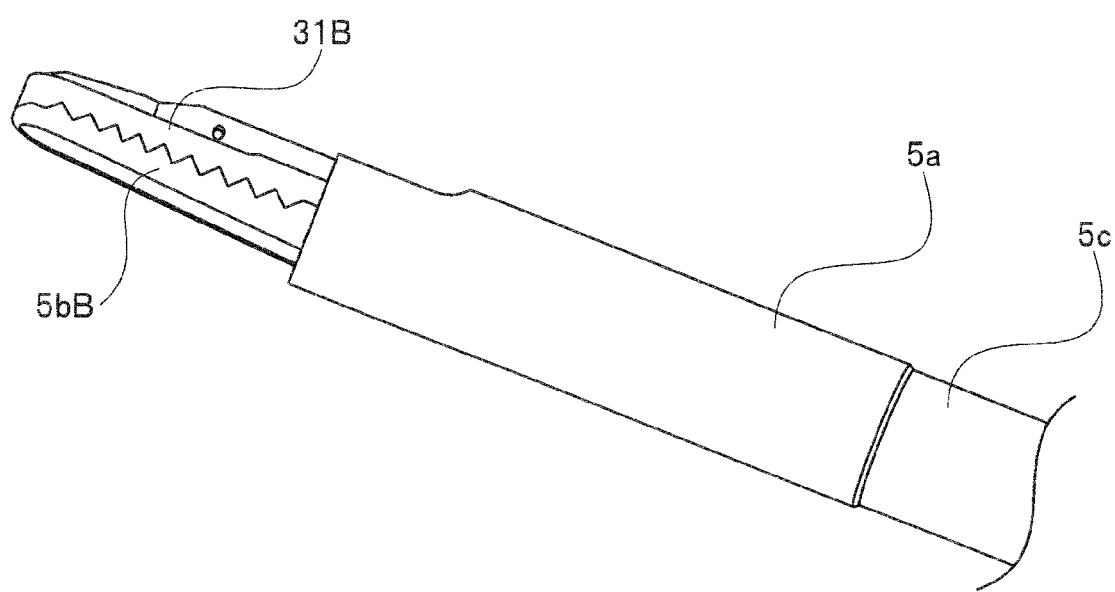
FIG. 18 is a side view of a hold unit of a handpiece in which a surface 31b of a movable jaw and a surface 5b1 of the fixed electrode 5b have respective concavo-convex portions.

Furthermore, as a variation of the movable jaw and fixed electrode, the surface 31b of the movable jaw and the surface 5b1 of the fixed electrode 5b do not need to be flat. FIG. 18 is a side view of a hold unit of a handpiece in which the surface 31b of the movable jaw and the surface 5b1 of the fixed electrode 5bB have respective concavo-convex portions.

As shown in FIG. 18, concavo-convex portions are formed on respective opposing surfaces 31b and 5b1 of a movable jaw 31B and fixed electrode 5bB in the hold unit. The concavo-convex portions of the movable jaw 31B and fixed electrode 5bB are formed on the opposing surfaces 31b and 5b1 so as to mesh with each other when the movable jaw 31B is closed with respect to the fixed electrode 5bB. When viewed laterally, the concavo-convex portions are sawtooth-shaped.

Formation of the concavo-convex portions on the respective opposing surfaces 31b and 5b1 of the movable jaw 31B and fixed electrode 5bB in the hold unit provides the advantage of being able to reliably grasp the living tissue in the hold unit of the handpiece.

Second Embodiment

In the handpiece according to the first embodiment, the sheath member is detachable from the insertion portion, but a handpiece according to a second embodiment differs from the handpiece according to the first embodiment in that a sheath member is not detachable from the insertion portion. Otherwise the handpiece according to the second embodiment is identical to the handpiece according to the first embodiment.

Figure 19:
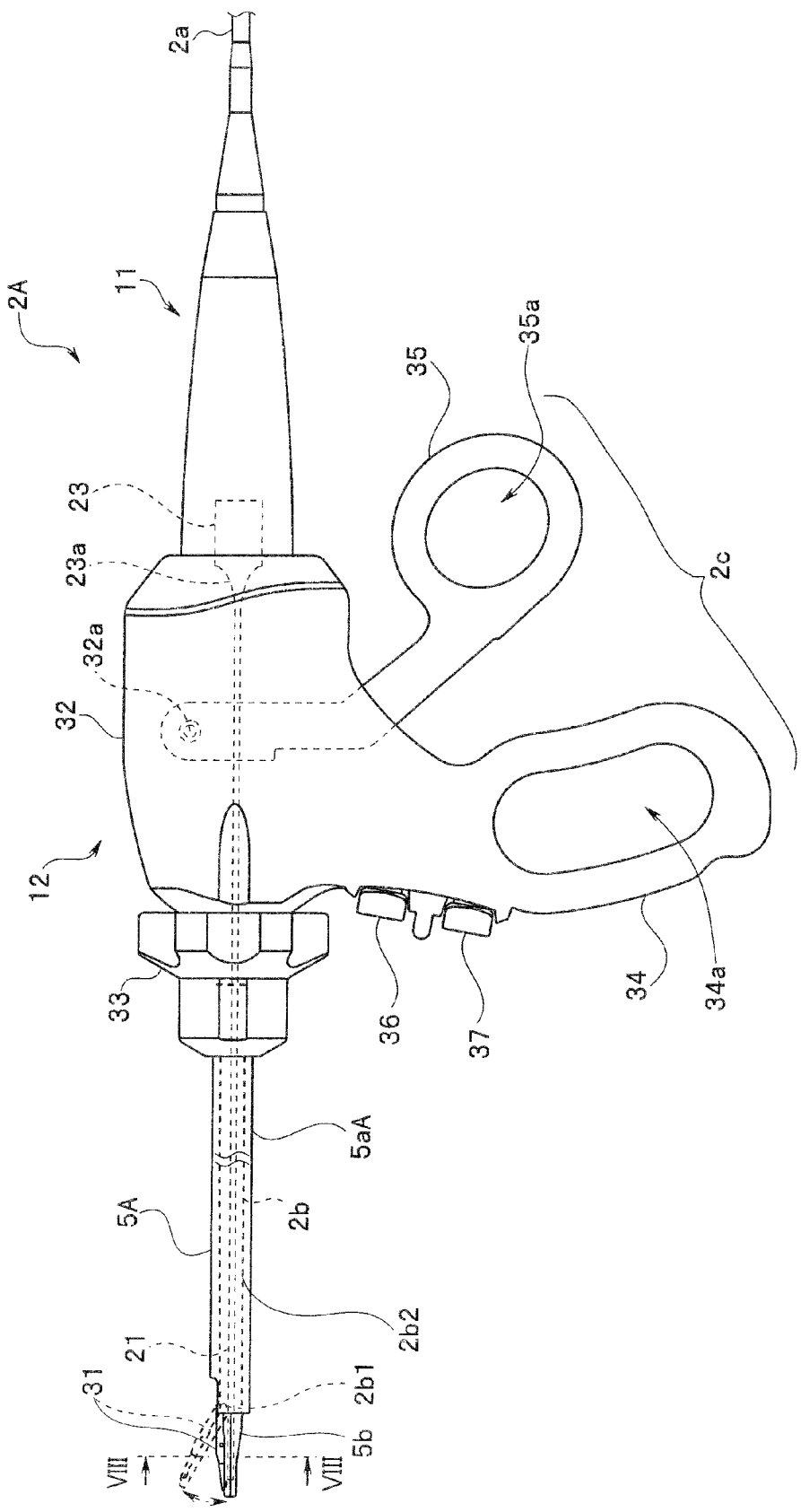
FIG. 19 is a diagram showing a configuration of a handpiece 2A according to a second embodiment of the present invention.

FIG. 19 is a diagram showing a configuration of the handpiece 2A according to the second embodiment of the present invention. In FIG. 19, the same components as those in FIG. 2 are denoted by the same reference numerals as the corresponding components in FIG. 2, and description thereof will be omitted. Also, since the handpiece 2A according to the second embodiment is substantially identical in configuration to the handpiece 2 according to the first embodiment, only different components will be described.

As shown in FIG. 19, a cylindrical body 5aA of a sheath member 5A is fixed to a distal end portion of the main operation unit 32. The sheath member 5A is not detachable from the main operation unit 32. A proximal end portion of sheath member 5A is electrically connected with an active line for high-frequency electric current output.

Thus, when a living tissue is coagulated and dissected simultaneously by simultaneously outputting high-frequency electric current and ultrasound vibration, the handpiece 2A according to the present embodiment delivers high sealing performance and makes it easy to visually check that surroundings of the dissection site have coagulated reliably, as in the case of the first embodiment.

Being configured to be connected with the probe 2b without using a pin, the handpiece 2A according to the second embodiment has the advantage of being simple in configuration as well.

The configuration according to any of the variations of the first embodiment is also applicable to the configuration of the second embodiment.

Thus, when a living tissue is coagulated and dissected simultaneously by simultaneously outputting high-frequency electric current and ultrasound vibration, the above-described embodiments and variations thereof can implement an energy treatment instrument which delivers high sealing performance and makes it easy to visually check that surroundings of the dissection site have coagulated reliably.

It should be noted that the present invention is not limited to the embodiments described above, and various changes and alterations are possible without departing from the spirit of the invention.

What is claimed is:

1. An energy treatment instrument comprising:
an electrically conductive probe having a first electrode in a distal end portion and adapted to transmit high-frequency electric current and ultrasound vibration to the first electrode;
a sheath member adapted to cover at least part of the probe;
an electrode member having two portions, each of the two portions being provided on one of both sides of a longitudinal axis of the first electrode separately from the electrically conductive probe, each of the two portions extending substantially in parallel to the first electrode in a distal end direction to form a second electrode; and
a movable member installed at a distal end of the sheath member and configured to be openable and closable with respect to the first electrode and the second electrode, wherein
the movable member is placed at a position facing the first electrode installed at the distal end of the probe and the second electrode and includes a third electrode provided with an electrode surface configured to be able to conduct high-frequency electric current between the third electrode and the first and second electrodes, the first electrode is provided with a planar, ultrasound processing surface and high-frequency current processing surfaces formed on both sides of the ultrasound processing surface and having two inclined surfaces, the movable member has an insulative pad member at a position to face the ultrasound processing surface, the third electrode is provided on both sides of the pad member, the movable member has two surfaces that oppose the two inclined surfaces of the high-frequency current processing surfaces of the first electrode, the two surfaces corresponding to the two inclined surfaces and being separated from the two inclined surfaces by a predetermined distance when the movable jaw is in a closed state with respect to the first electrode and the second electrode, and the second electrode is placed such that, when the movable member is brought into the closed state with respect to the first electrode and the second electrode, the first electrode and the pad member first come in contact with each other, and then an insulating member provided on the third electrode comes in contact with the second electrode, and when the insulating member and the second electrode are in contact with each other, a grasping force in a contact area between the insulating member and the second electrode is larger than a grasping force in a contact area between the first electrode and the pad member.

2. The energy treatment instrument according to claim 1, wherein:
   the second electrode is installed in a distal end portion of the sheath member; and
   the sheath member includes a fitting unit used to detachably fit the sheath member over the probe.

3. The energy treatment instrument according to claim 2, wherein when the sheath member is fitted over the probe, the fitting unit comes into contact with a member installed at a node position of ultrasound vibration performed by the probe and thereby supplies the high-frequency electric current from the probe to the second electrode.

4. The energy treatment instrument according to claim 3, further comprising
   an electrically conductive lining installed on an outer circumference of the probe, wherein
   the high-frequency electric current from the probe is supplied to the second electrode via the lining.

5. The energy treatment instrument according to claim 1, wherein
   the two portions are coupled to each other at respective distal ends via a coupling unit.

* * * * *